United States Patent [19]

Roussel et al.

[11] Patent Number: 5,770,748
[45] Date of Patent: Jun. 23, 1998

[54] INTERMEDIATE STEROID COMPOUND

[75] Inventors: Patrick Roussel, Thiais; Michel Vivat, Lagny Sur Marne, both of France

[73] Assignee: Roussel Uclaf, France

[21] Appl. No.: 758,951

[22] Filed: Dec. 2, 1996

Related U.S. Application Data

[62] Division of Ser. No. 519,772, Aug. 28, 1995, Pat. No. 5,650,526.

[30] Foreign Application Priority Data

Sep. 6, 1994 [FR] France ................................. 94-10661

[51] Int. Cl.$^6$ ..................................................... C07J 31/00
[52] U.S. Cl. ............................................................ 552/531
[58] Field of Search ............................................... 552/531

[56] References Cited

U.S. PATENT DOCUMENTS 4,389,345  6/1983  Lenz ........................................ 552/531

*Primary Examiner*—Rebecca Cook
*Attorney, Agent, or Firm*—Bierman, Muserlian and Lucas

[57] ABSTRACT

A novel process for the preparation of oxoetiocholenic acid of the formula

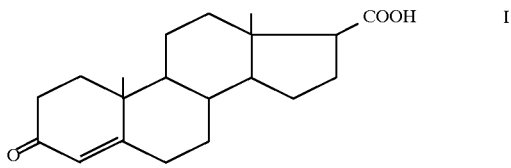

and intermediates therefore.

1 Claim, No Drawings

INTERMEDIATE STEROID COMPOUND

This application is a division of U.S. patent application Ser. No. 519,772 filed Aug. 28, 1995, now U.S. Pat. No. 5,650,526.

OBJECTS OF THE INVENTION

It is an object of the invention to provide a novel process for the preparation of oxoetiocholenic acid and novel intermediates therefore.

These and other objects and advantages of the invention will become obvious form the following detailed description.

THE INVENTION

The novel process of the invention of oxoetiocholenic acid of the formula

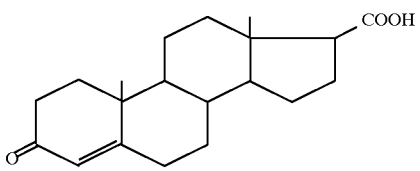

comprises reacting a compound of the formula

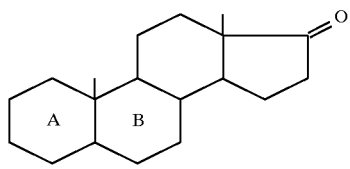

wherein the A and B rings are selected from the group consisting of

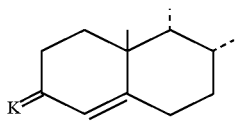

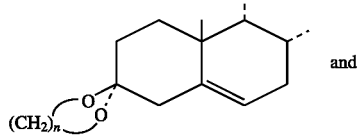

and

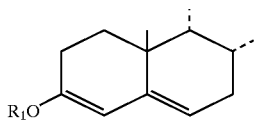

K is an oxo protective group selected from the group consisting of

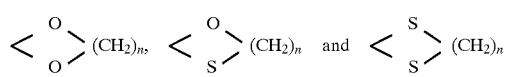

wherein n is 2 or 3, and $R_1$ is an ether or ester with a halonitrile in the presence of a base to obtain a compound of formula

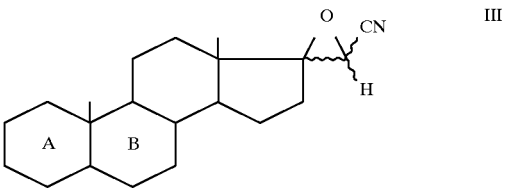

wherein rings A and B have the above definition and the wavy lines indicate a mixture of isomers, reacting the latter to free the 3-ketone to obtain a compound of the formula

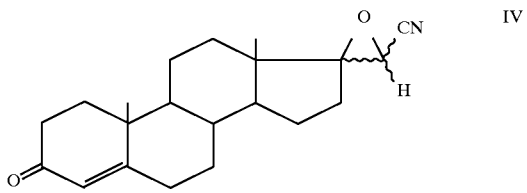

wherein the wavy lines have the above meaning, reacting the latter with an acid of the formula HX in which X is halogen in an anhydrous medium to obtain a compound of the formula

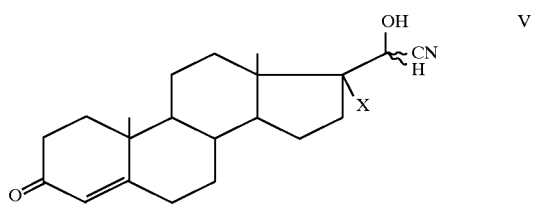

in which X and the wavy lines have the above meaning, protecting the hydroxy in the form of an ester to obtain a compound of the formula

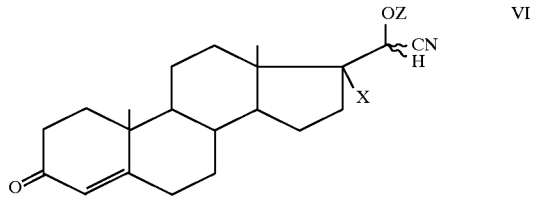

wherein Z is a protective ester group of the hydroxy and X and the wavy lines have the above meaning, subjecting the latter to the action of a dehydrohalogenation agent to obtain the compound of the formula

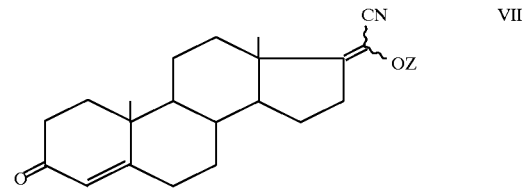

wherein Z and the wavy lines have the above meaning, subjecting the latter to an alkaline hydrolysis, then to an acid treatment to obtain the compound of formula I.

Examples of $R_1$ as an ether are alkyl of 1 to 6 carbon atoms, alkoxyalkoxyalkyl of 3 to 8 carbon atoms, aryl of 6 to 10 carbon atoms or aralkyl of 7 to 12 carbon atoms.

When $R_1$ is alkyl, it is preferably methyl, ethyl, propyl, isopropyl, n-butyl, sec-butyl, tert-butyl, pentyl or hexyl. When $R_1$ is alkoxyalkoxyalkyl, it is preferably methoxyethoxymethyl and when $R_1$ is aralkyl, it is for example benzyl or phenethyl. When $R_1$ is aryl, it is preferably phenyl or phenyl substituted by one or more alkyls.

When $R_1$ is an ether, it can also be a silylated group such as trialkylsilyl like trimethylsilyl, tert-butyldimethylsilyl or a triarylsilyl such as triphenylsilyl or diarylalkylsilyl such as diphenyl tert-butylsilyl.

When $R_1$ forms an ester, it can be any ester group known to one skilled in the art for blocking the 3- position in this form and particularly it can be —$COR_1$, $R_1$ being alkyl, aryl or aralkyl as defined above.

A particular subject of the invention is a process as defined previously characterized in that a starting compound of formula II is used in which rings A and B are

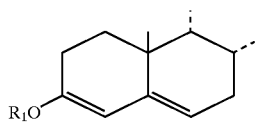

wherein $R_1$ is defined as previously and particularly alkyl of 1 to 6 carbon atoms.

The halonitrile which is reacted with the compound of formula II can be bromoacetonitrile or preferably chloroacetonitrile. The operation is carried out in the presence of a strong base, preferably non-nucleophilic, such as an alcoholate, a hydride, an amide or a hydroxide of an alkali metal, or an organolithium compound such as the methylate, the ethylate, the terbutylate or the teramylate of sodium or potassium, lithium diisopropylamide, or also sodium hydroxide or potassium hydroxide.

It may be advantageous to operate in heterogeneous phases in the presence of a phase transfer catalyst which can be a quaternary ammonium salt such as tetrabutylammonium bromide, triethylbenzylammonium chloride or tricaprylmethylammonium chloride, or a phosphonium salt. An alcoholate is preferably used such as the terbutylate or teramylate of potassium or sodium.

The reaction is carried out in an organic solvent such as toluene, dichloromethane, dimethoxyethane, dimethylformamide, tetrahydrofuran or a mixture of these solvents, for example a toluene/tetrahydrofuran mixture or a terbutanol/tetrahydrofuran mixture.

The release of the 3-ketone function is carried out by means appropriate to the nature of the protective group. An acid agent is used in the presence of water or a water-alkanol mixture in the case of a ketal. It is for example a mineral or organic acid such as hydrochloric acid, hydrobromic acid, sulfuric acid, perchloric acid, nitric acid, p-toluene sulfonic acid, acetic acid, formic acid, oxalic acid or a mixture of acids, or also an acid resin, for example a sulfonic acid resin. In the case of a thioketal or a mixed ketal, the deprotection of the 3-oxo is carried out by the action of iodine in the presence of a base such as an alkali metal bicarbonate, or by the action of iodine in catalytic quantity in the presence of an oxidizing agent, particularly hydrogen peroxide, by the action of methyl iodide, glyoxylic acid, or also salts of metals such as mercury or cadmium. The operation can generally be carried out in a solvent such as a lower alkanol, for example methanol or ethanol, mixed with a halogenated solvent, for example methylene chloride in the presence of water. In the case of a mixed ketal, the deprotection is also carried out for example by a mercuric salt such as mercuric chloride in the presence of an acetic acid/potassium acetate buffer at about 100° C., by Raney nickel under the same conditions as above or by a hot hydrochloric acid - acetic acid mixture.

In the case where $R_1$ is an ether or ester, an acid treatment is also used under the conditions described above for the ketal. There can be used for example acetic acid or sulfuric acid or a mixture of these acids.

The HX which is used for opening the epoxide function can be for example hydrobromic acid or, preferably, hydrochloric acid. The reaction is preferably carried out in an anhydrous medium in an organic solvent, preferably only slightly polar or non-polar, such as dimethoxyethane, ethyl ether, ethyl acetate, dichloromethane or toluene, these last two being preferred. The operation is advantageously carried out in the presence of a tertiary amine such as pyridine or triethylamine.

The protection of the 20-hydroxy function in the form of an ester can be carried out by the usual methods using a carboxylic acid derivative and in particularly a halide or an anhydride of an alkanoic or aromatic acid, preferably in the presence of a nitrogenous base. There can be used for example acetic acid, propionic acid, valeric acid or benzoic acid anhydride in the presence of pyridine.

The dehydrohalogenation is carried out by the action of a base such as a tertiary amine such as triethylamine or pyridine, or of a non-nucleophilic base such as lithium carbonate - lithium bromide, sodium hydroxide or potassium hydroxide. The reaction is carried out in a non-hydrophilic organic solvent such as dichloro-methane, dimethylformamide, dimethylsulfoxide or, preferably, toluene. The operation is advantageously carried out at reflux of the reaction medium.

The alkaline hydrolysis is carried out using a strong base, particularly barium hydroxide, potassium hydroxide, sodium carbonate, or preferably sodium hydroxide. The operation is carried out in the presence of water or a water - alcohol mixture which stabilizes the basic salt formed, if appropriate in a double-phase system, with the solvent in which the preceding stage has been carried out.

Isolation of oxoetiocholenic acid is carried out by acid treatment of the basic salt by the usual methods, for example using a mineral acid such as sulfuric acid or hydrochloric acid.

A particular subject of the invention is a process as defined previously, characterized in that the operation is carried out without intermediately isolating the compounds of formula IV and the subsequent compounds.

Also a subject of the invention as new intermediates for the process of the invention are compounds of the formula

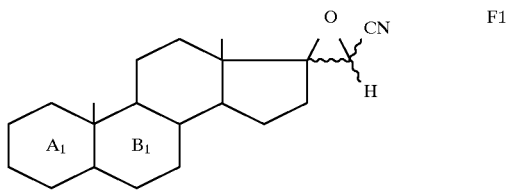

in which rings A1 and B1 have the meaning indicated for rings A and B, or

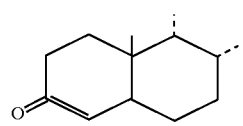

and the wavy lines have the above meaning, the compounds of the formula

F2 in which X and the wavy lines have the meaning indicated previously and Z' is hydrogen or a protective ester group of the hydroxy and the compounds of the formula

VII in which Z and the wavy lines have the above meaning.

The compound of formula II is described in French Patent 1,563,607.

The acid of formula I or oxoetiocholenic acid is a product known particularly as a synthesis intermediate and described, for example, in European Application 562,849.

In the following examples, there are described several preferred embodiments to illustrate the invention. However, it should be understood that the invention is not intended to be limited to the specific embodiments.

EXAMPLES

Example 1: 17β-Δ$^4$-androstene-3-one: oxoetiocholenic acid

STAGE A: 17,20-epoxy-3-methoxy-17α-Δ$^{3,5}$-pregnadiene-21-nitrile 15 g of 3-methoxy-Δ$^{3,5}$-androstadiene-17-one in 120 ml of tetrahydrofuran and 5.5 g of terbutanol were cooled to −45° C. under an inert gas atmosphere and then 9 g of potassium terbutylate were added. Then, over 4 hours at about −45° C., 4.8 g of chloroacetonitrile dissolved in 30 ml of tetrahydrofuran were added. The reaction mixture was introduced under an inert gas atmosphere into a solution cooled to 0° C. of 2 g of ammonium chloride in 300 ml of water. Then, the mixture was maintained with stirring for 30 minutes. It was filtered, washed with methanol with 20% water and the residue was taken up in 15 ml of an 1–2 isopropanol/isopropyl ether mixture, followed by separating and washing again with 30 ml of the above mixture. After separation and drying under reduced pressure, 13.4 g of the expected product melting at 180° C. were obtained.

| IR spectrum (CHCl$_3$) | |
| --- | --- |
| conj. C=C | 1654–1629 cm$^{-1}$ |
| C≡N | 2248 cm$^{-1}$ |
| NMR spectrum (CDCl$_3$ ppm) | |
| 0.94 | CH$_3$ in position 18 |
| 0.98 | CH$_3$ in position 19 |
| 3.49 | CH in position 20 |
| 3.58 | CH$_3$ in position 3 |
| 5.14 (d) | CH in position 4 |
| 5.25 (d) | CH in position 6 |

STAGE B: 17β-carboxy-Δ$^4$-androstene-3-one: oxoetiocholenic acid

1) Hydrolysis of the enol ether in position 3

64 ml of acetic acid, 13 ml of water and 13 ml of dilute sulfuric acid (2N) were added under an inert atmosphere to 12.85 g of 17,20-epoxy-3-methoxy-17α-Δ$^{3,5}$-pregnadiene-21-nitrile prepared in Stage A. The reaction mixture was stirred for 90 minutes at ambient temperature and 64 ml of toluene and 64 ml of water were added over 10 minutes, followed by decanting. The toluene phase was washed with water, then with a 2% aqueous solution of sodium bicarbonate, and the toluene was distilled off under 150/100 mbars until a volume of about 25 ml was obtained.

2) Opening of the epoxide 100 ml of dichloromethane and 6 ml of pyridine were added under an inert atmosphere to the above reaction medium, followed by cooling to −5° C. Gaseous hydrochloric acid was introduced over about 3 hours and the mixture was stirred for one hour at −5° C. The excess hydrochloric acid was neutralized by addition of 21.5 ml of pyridine.

3) Acetylation of the chlorhydrin

The temperature of the above suspension was allowed to return to about +10° C. and then over 30 minutes, 7.8 ml of acetic anhydride and 6 ml of pyridine were added. The reaction mixture was stirred for 16 hours at ambient temperature, followed by washing with water and decanting. The residue was distilled under 400 to 150 mbars until a crystallized crude product was obtained.

4) 17–20 elimination of the acetate derivative 50 ml of toluene and 25 ml of triethylamine were added under an inert atmosphere to the above product and the mixture was refluxed for 3 hours and 30 minutes and then allowed to return to ambient temperature.

5) Hydrolysis of the enol acetate 50 ml of water and 25 ml of sodium hydroxide were added under an inert atmosphere to the reaction medium prepared previously and the mixture was stirred for 20 hours. 250 ml of water were added and the aqueous phase was decanted.

6) Acidification of the sodium salt/preparation of the acid

The aqueous phase was cooled to +10°/+15° C. under a nitrogen atmosphere and 80 ml of dilute sulfuric acid (4N) were added with stirring. The gaseous hydrocyanic acid was driven off by sweeping with an inert gas and the precipitate formed was filtered off, washed with water and dried under reduced pressure to obtain 9.33 g of the expected product melting at 255°–256° C.

| IR spectrum (CHCl$_3$) | |
| --- | --- |
| C=O | 1702 cm$^{-1}$ |
| Δ$^4$-3-one | 1662–1615 cm$^{-1}$ |
| NMR spectrum (CDCl$_3$ ppm) | |
| 0.79 | CH$_3$ in position 18 |
| 1.19 | CH$_3$ in position 19 |
| 5.74 | CH in position 4 |

Example 2: 17β-carboxy-Δ$^4$-androstene-3-one: oxoetiocholenic acid

STAGE A: 17,20-epoxy-17α-Δ$^4$-pregnene-3-one-21-nitrile 1.017 g of the product obtained in Stage A of Example 1 were mixed for 3 hours at 20° C. under an inert gas atmosphere with 10 ml of acetic acid and 5 ml of water and 4 ml of tetrahydrofuran were added. The mixture was stirred for 2 hours and the solvents were evaporated off under reduced pressure. The residue was chromatographed on silica (eluant: toluene - ethyl acetate 8-2) to obtain 691 mg of the expected product.

| IR spectrum (CHCl$_3$) | |
| --- | --- |
| C≡N | 2240 cm$^{-1}$ |
| C=O | 1662 cm$^{-1}$ |
| C=C | 1617 cm$^{-1}$ |
| NMR spectrum (CDCl$_3$ ppm) | |
| 0.95 | CH$_3$ in position 18 |
| 1.20 | CH$_3$ in position 19 |
| 3.32–3.48 | CH in position 20 |
| 5.75 | CH in position 4. |

STAGE B1: 17α-chloro-Δ$^4$-pregnene-3-oxo-20-ol-21-nitrile 1 g of the product of Stage A was added to 2 ml of a 4.7N solution of gaseous hydrochloric acid in 4.7N solution of gaseous hydrochloric acid in 4.7N dimethoxyethane cooled to +5°/+10° C. and the mixture was stirred for 3 hours. A further 1 ml of reagent was added, followed by stirring for one hour while maintaining the temperature at 10° C. and the reaction mixture was used as is for the following stage.

STAGE B2: 17α-chloro-20-acetoxy-Δ$^4$-pregnene-3-one-21-nitrile 0.25 g of the epoxide of Stage A dissolved in 10 ml of dichloromethane and 0.1 ml of pyridine was stirred under an inert atmosphere. A current of gaseous hydrochloric acid was introduced slowly at about 20° C. for one hour and the excess hydrochloric acid was eliminated by sweeping with an inert gas. Half of the reaction medium was used as is for following stage and the other half was washed with water and dried. The solvent was evaporated under reduced pressure and the residue was taken up in 2 ml of an ethanol-water mixture (1-1), followed by triturating, separating, washing with water and drying under reduced pressure to obtain 0.1 g of the expected product melting at 230°–240° C. (decomp.).

| NMR spectrum (CDCl$_3$ ppm) | |
| --- | --- |
| 0.97–0.98 | CH$_3$ in position 18 |
| 1.21 | CH$_3$ in position 19 |
| 3.05–3.22 | OH in position 20 |
| 4.56–4.77 | CH in position 20 |
| 5.75 | CH in position 4. |

STAGE C: 20-acetoxy-17α-chloro-Δ$^4$-pregnene-3-one-21-nitrile 3 ml of dimethoxyethane were added to the reaction medium of Stage B1 cooled to 10° C. and then 1.7 ml of pyridine and 1 ml of acetic anhydride were added over a few minutes. The reaction medium was allowed to return to ambient temperature over one hour and 0.8 ml of pyridine and 5 ml of water were added. The mixture stood at +4° C. for 16 hours and the precipitate formed was separated off, washed with dimethoxyethane and dried under reduced pressure to obtain 0.364 g of the expected product melting at 238° C.

| IR spectrum (CHCl$_3$) | |
| --- | --- |
| OAc | 1757 cm$^{-1}$ |
| Δ$^4$-3-one | 1665–1616 cm$^{-1}$ |
| NMR spectrum (CDCl$_3$ ppm) | |
| 1.04 | CH$_3$ in position 18 |
| 1.21 | CH$_3$ in position 19 |
| 2.22 | O—Ac |
| 5.74 | CH in position 4 and in position 20. |

STAGE D: (E+Z) 20-acetoxy-Δ$^{4,17(20)}$-pregnadiene-3-one-21-nitrile 0.5 ml of toluene and 0.2 ml of triethylamine were added to 100 mg of the product obtained of Stage C under an inert atmosphere. The mixture was refluxed for 5 hours, then cooled to 10° C. The precipitate was separated off, washed with toluene, then with water and dried under reduced pressure to obtain 91 mg of the expected product melting at 185°–190° C.

| IR spectrum (CHCl$_3$) | |
| --- | --- |
| C≡N (conj) | 2223 cm$^{-1}$ |
| OAc | 1773 cm$^{-1}$ |
| Δ$^4$-3-one | 1662–1616 cm$^{-1}$ |
| NMR spectrum (CDCl$_3$ ppm) | |
| 0.97 | CH$_3$ in position 18 |
| 1.19 | CH$_3$ in position 19 |
| 2.20 | O—Ac |
| 5.74 | CH$_3$ in position 4. |

STAGE E: 17β-carboxy-Δ$^4$-androstene-3-one: oxoetiocholenic acid

Using the procedure of Stages B5 and B6 of Example 1, the product obtained in Stage D was reacted to obtain the expected oxoetiocholenic acid.

Various modifications of the process of the invention may be made without departing from the spirit or scope thereof and it is to be understood that the invention is intended to be limited only as defined in the appended claims.

What we claim is:

1. A compound having a formula

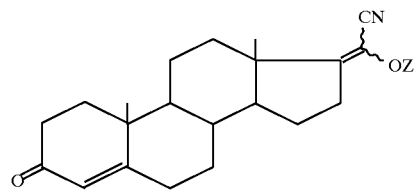

VII

Z is a protective ester group of hydroxy and the wavy lines indicate a mixture of isomers.

* * * * *